United States Patent
Lee et al.

(10) Patent No.: US 10,963,547 B2
(45) Date of Patent: Mar. 30, 2021

(54) WEARABLE DEVICE FOR TRUSTED BIOMETRIC IDENTITY

(71) Applicant: Securiport LLC, Washington, DC (US)

(72) Inventors: Chi Jung Lee, Burke, VA (US); Frank Buscaglio, Gaithersburg, MD (US)

(73) Assignee: Securiport LLC, Washington, DC (US)

( * ) Notice: Subject to any disclaimer, the term of this patent is extended or adjusted under 35 U.S.C. 154(b) by 190 days.

(21) Appl. No.: 16/033,945

(22) Filed: Jul. 12, 2018

(65) Prior Publication Data
US 2020/0019682 A1 Jan. 16, 2020

(51) Int. Cl.
| | |
|---|---|
| G06F 21/32 | (2013.01) |
| A61B 5/00 | (2006.01) |
| G06K 9/00 | (2006.01) |
| H04L 29/06 | (2006.01) |
| H04W 12/06 | (2021.01) |
| G06F 1/3231 | (2019.01) |
| G06F 1/16 | (2006.01) |
| G06F 21/35 | (2013.01) |

(52) U.S. Cl.
CPC .............. *G06F 21/32* (2013.01); *A61B 5/681* (2013.01); *G06K 9/00892* (2013.01); *H04L 63/0853* (2013.01); *H04L 63/0861* (2013.01); *H04W 12/06* (2013.01); *G06F 1/163* (2013.01); *G06F 1/3231* (2013.01); *G06F 21/35* (2013.01); *G06K 2009/00939* (2013.01)

(58) Field of Classification Search
CPC ..... G06F 21/32; A61B 5/681; G06K 9/00892; H04L 63/0853
See application file for complete search history.

(56) References Cited

U.S. PATENT DOCUMENTS

| | | | |
|---|---|---|---|
| 8,083,130 B1* | 12/2011 | Cipriano | H04L 63/123 235/375 |
| 9,558,336 B2 | 1/2017 | Lee | |
| 9,648,015 B1 | 5/2017 | Avetisov et al. | |
| 2003/0173408 A1* | 9/2003 | Mosher, Jr. | G06K 19/07749 235/492 |
| 2005/0040944 A1* | 2/2005 | Contestabile | G08B 21/028 340/539.13 |

(Continued)

*Primary Examiner* — Vance M Little
(74) *Attorney, Agent, or Firm* — Brake Hughes Bellermann LLP

(57) ABSTRACT

A wearable device may store a biometric token associated with a wearer of the wearable device, the wearable device including: a wireless communications interface; a processing circuitry; a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; an invalidating event detector configured to determine if an invalidating event has occurred; wherein the processing circuitry is configured to invalidate the biometric token in response to detecting that an invalidating event has occurred for the biometric token.

34 Claims, 6 Drawing Sheets

(56) References Cited

U.S. PATENT DOCUMENTS

| | | | |
|---|---|---|---|
| 2006/0059548 A1* | 3/2006 | Hildre | H04L 9/3234 726/9 |
| 2008/0320600 A1* | 12/2008 | Pandiscia | H04L 9/3297 726/27 |
| 2014/0089672 A1* | 3/2014 | Luna | H04L 9/3231 713/186 |
| 2014/0101453 A1* | 4/2014 | Senthurpandi | G06F 21/32 713/172 |
| 2015/0028996 A1 | 1/2015 | Agrafioti et al. | |
| 2015/0186636 A1 | 7/2015 | Tharappel et al. | |

* cited by examiner

Example Verification

WEARABLE DEVICE FOR TRUSTED BIOMETRIC IDENTITY

BACKGROUND

Wearable technology is growing in popularity. There are a wide variety of wearable devices that are now available, such as smart watches (e.g., which may include a processor, memory, a display, and wireless interface), activity (or fitness) trackers (e.g., to track steps taken, calories burned, time spent exercising), eyewear with a heads-up display, health monitoring devices (e.g., to monitor a variety of health conditions or status of the wearer, such as to track heartrate, pulse, temperature, blood pressure). Some of these wearable devices include technology that would typically be provided in a phone or computer, such as a processor, a memory, a wireless interface, a display, and one or more applications running thereon. However, wearable devices are usually, by design, small, lightweight, stylish, and limited in capability.

SUMMARY

The details of one or more implementations are set forth in the accompanying drawings and the description below. Other features will be apparent from the description and drawings, and from the claims.

According to an implementation, a method of managing a biometric token that is provided on a wearable device is provided, including storing, in a memory of the wearable device, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; detecting, by an invalidating event detector provided on the wearable device, that an invalidating event has occurred; and invalidating the biometric token in response to detecting that the invalidating event has occurred for the biometric token.

According to an implementation, a non-transitory computer readable medium storing executable instructions that when executed by at least one processor is configured to store, in a memory of the wearable device, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; detect, by an invalidating event detector provided on the wearable device, that an invalidating event has occurred; and invalidate the biometric token in response to detecting that the invalidating event has occurred for the biometric token.

According to an implementation, a wearable device is configured to store a biometric token associated with a wearer of the wearable device, the wearable device including: a wireless communications interface; a processing circuitry (e.g., a processor); a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; an invalidating event detector configured to determine if an invalidating event has occurred; wherein the processing circuitry is configured to invalidate the biometric token in response to detecting that an invalidating event has occurred for the biometric token.

According to an implementation, a wearable device is configured to store a biometric token associated with a wearer of the wearable device, the wearable device including: a wireless communications interface; a processing circuitry; a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; a detachment sensor that is configured to detect if the wearable device becomes detached from the wearer; wherein the processing circuitry is configured to invalidate the biometric token in response to detecting that the wearable device was detached from the wearer.

According to an implementation, a wearable device is configured to store a biometric token associated with a wearer of the wearable device, the wearable device including: a wireless communications interface; a processing circuitry; a memory configured to store information indicating a permitted geographic area associated with the wearer, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; a location detector configured to determine a location of the wearable device; wherein the processing circuitry is configured to: compare a location of the wearable device to the permitted geographic area associated with the wearer; detect that the location of the wearable device is outside of the permitted geographic area associated with the wearer; and invalidate the biometric token in response to detecting that the location of the wearable device was outside of the permitted geographic region.

DETAILED DESCRIPTION

Figure 1:
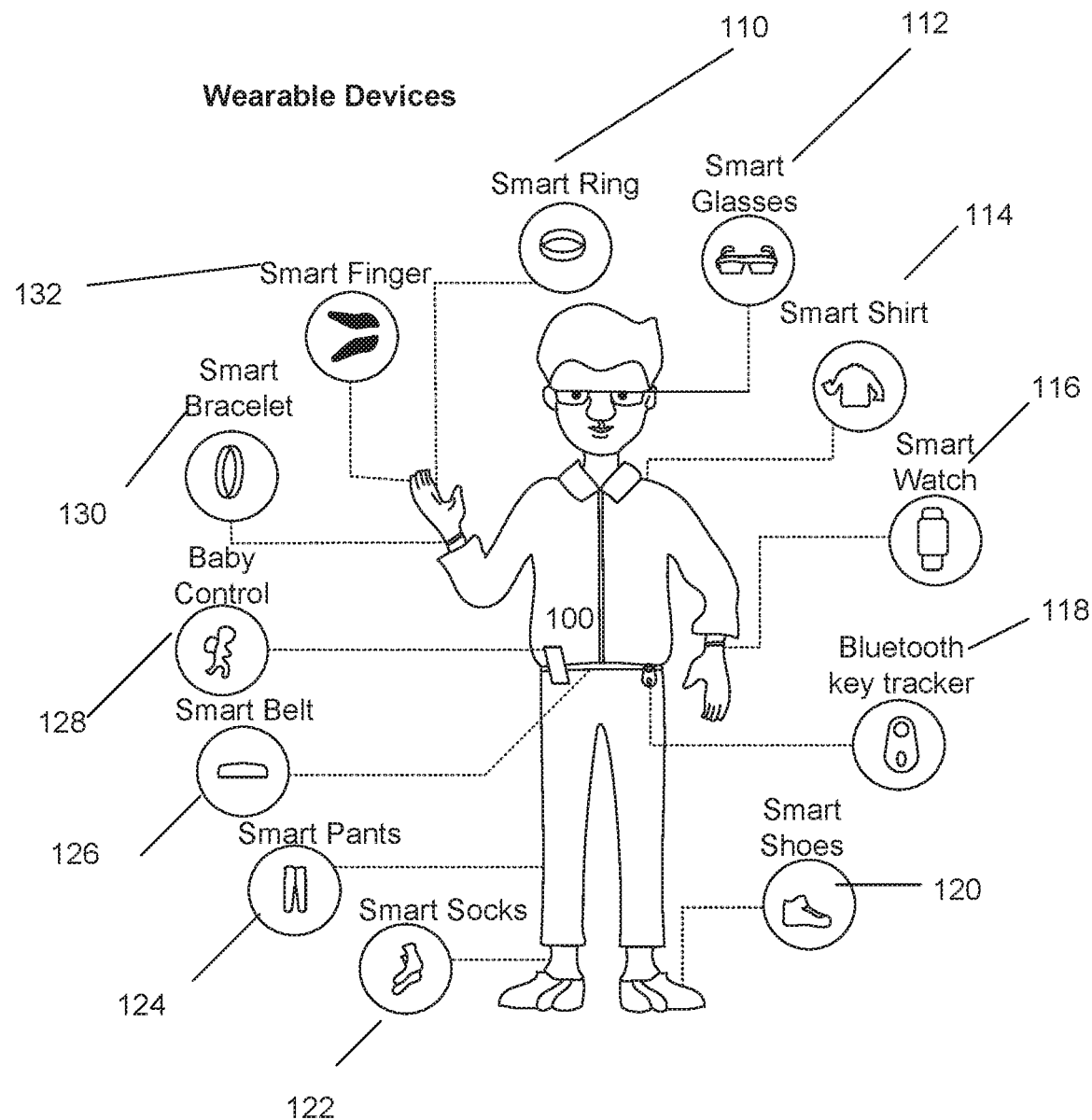
FIG. 1 is a diagram illustrating some example wearable devices according to an example embodiment.

Because wearable devices are typically small and limited in capabilities, it may be difficult, impractical, visually unappealing, and/or prohibitively expensive to embed or include a biometric scanning device(s) (e.g., fingerprint readers, iris scanners, palm readers and the like) into a wearable device such as a ring or bracelet. For example, it may be desirable to maintain biometric information on the wearable device without requiring the wearable device to scan or collect the biometric scans/data. Furthermore, in some cases, an identity of the wearable device may be established by associating the device identifier (ID) and some login credentials with a set of data on the device or stored in an external database. This does not prevent the wearable device from being used by another individual. For example, a criminal may clone or duplicate an RFID (radio frequency identifier) wristband to unlock someone else's door, or someone may use another's lost smart watch to purchase an item before the owner reports the smart watch as lost.

According to an example embodiment, wearable security may be improved by providing techniques to manage the trust of information stored on the wearable device, e.g., based on whether the device is still under control of the verified owner, and/or more generally based on whether the wearer of the wearable device has remained in compliance with policies established to manage use of the wearable device.

According to an example embodiment, a biometric token may include information, e.g., biometric patterns based on biometric scan(s) of a person (such as a wearer of the device) and other data, which may be associated with the wearer. According to an example embodiment, the biometric token may be stored on a wearable device that is associated with a person (such as the wearer of the wearable device). For example, a unique key may be stored, so that all the information may be stored in a database (associated with the unique key o reference number), and some or part of the information may also be stored on a device.

Thus, according to an example embodiment, a wearable device, such as a wristband, a ring, or other wearable device, may include a biometric token stored thereon. The biometric token may be associated with the wearer (e.g., the biometric token may be based on or may include biometric scans or patterns of the wearer and/or the biometric token may be based on or may include wearer identifying information (e.g., passport, VISA, driver's license, national ID, . . . ). If the biometric token is marked or indicated as valid, this establishes trust for the data (e.g., biometric patterns and/or wearer identifying information, and/or other data) stored on the wearable device, and thus, indicating reliability or trust that such data identifies or is associated with the wearer of the wearable device, and thus, reliably confirming identity of the wearer.

Also, according to an example embodiment, if an invalidation event is detected by the wearable device (e.g., a use of the device is detected that violates the established policy for the use of the wearable device, such as the wearable device being removed from the wearer, or being tampered with, etc.), then the biometric token is invalidated (e.g., and the biometric token is marked or indicated as invalid), which removes the trust in the data stored on the wearable device. Thus, for example, if an invalidating event has been detected for the wearable device, it cannot be trusted that the data (e.g., biometric patterns or wearer identifying documents) stored on the wearable device are associated with (e.g., identify) the wearer of the wearable device.

According to an aspect, some example implementations discussed herein provide a wearable device that is configured to store a biometric token associated with a wearer of the wearable device. In an example embodiment, the wearable device may include, for example, a wireless communications interface, a processing circuitry (e.g., a processor), a memory configured to store a biometric token associated with a wearer of the wearable device. The biometric token may include, for example, a device identifier that is associated with the wearable device, a biometric template for each of one or more biometric scans of the wearer of the wearable device, and an indication of whether or not the biometric token is valid. If the biometric token is valid, this establishes a trust that the biometric patterns (or biometric information) stored on the wearable device and/or wearer identifying information (e.g., Passport, a VISA, a driver's license, a National identification (ID) card, a ticket or pass assigned to the wearer of the wearable device, or other information associated with or identifying the wearer), linked to the biometric token, is associated with (e.g., identifies) the wearer.

The wearable device may also include an invalidating event detector configured to determine if an invalidating event has occurred. In an example embodiment, the processing circuitry (e.g., processor) may be configured to invalidate the biometric token in response to detecting that an invalidating event has occurred for the biometric token. Also, the wearable device may include a display or other visual indicator that indicates whether the biometric token stored on the wearable device is valid or invalid (e.g., a visual valid/invalid indicator on a display or other visual indicator).

In an example embodiment, the invalidating event detector may be configured to determine (or detect) an occurrence of one or more invalidating events for the biometric token, including being configured to detect one or more of the following invalidating events of: that a time-to-live (or lifetime, or valid time period) for the biometric token has expired; that a location of the wearable device has traveled to or been located at a location that is outside of a permitted geographic area for the biometric token (e.g., outside of a geographic fence or permitted geographic area); that the wearable device has become detached from the wearer; the electronics or processor of the wearable device has been shut-down and powered back up (e.g., it may be possible in some cases that the wearable device may have been detached from an original wearer or person, and then re-attached to a different wearer or person while powered down or shut down); the wearable device has been tampered with; a failed validation attempt, or other invalidating event.

Thus, for example, the processing circuitry (e.g., processor) of the wearable device may update a status (e.g., a state or flag stored in memory indicating either a valid or invalid biometric token) of the biometric token from valid to invalid if an invalidating event detector detects an invalidating event. For example, the processing circuitry or processor may update a status (of the biometric token) in memory to invalid in response to a detachment sensor detecting that the wearable device was detached from the wearer, or in response to detecting that the wearable device has been shut-down and powered back up, tampered with, or traveled to a location that is outside of permitted geographic region or geographic fence for the wearer or wearable device (or biometric token).

According to an example embodiment, the invalidating event detector may include a detachment sensor that is configured to detect if the wearable device becomes detached from the wearer, and the processing circuitry or processor is configured to invalidate the biometric token in response to detecting that the wearable device was detached from the wearer.

In yet another example embodiment, the invalidating event detector may include a location detector configured to determine a location of the wearable device, and where the processing circuitry is configured to: compare a location of the wearable device to a permitted geographic area associated with the wearer or the biometric token; detect that the location of the wearable device is outside of the permitted geographic area; invalidate the biometric token in response to detecting that the location of the wearable device was outside of the permitted geographic region.

In response to detecting an invalidating event, the processing circuitry may invalidate the biometric token, e.g., based on performing at least one of the following: store information in the memory indicating that the biometric token is invalid (e.g., change a state of a valid/invalid flag stored in memory of the wearable device to invalid to indicate that the biometric token is invalid); and/or delete, from the memory, at least a portion of the biometric token so as to render to biometric token invalid.

FIG. 1 is a diagram illustrating some example wearable devices according to an example embodiment. According to an example embodiment, a wearer (a person wearing a wearable device) 100 may wear any number of wearable devices. For example, a wearable device may include a smart ring 110, smart glasses 112, a smart shirt 114, a smart watch 116, a Bluetooth key tracker 118, smart shoes 120, smart socks 122, smart pants 124, a smart belt 126, a smart baby carrier 128, a smart bracelet 130, and a smart finger device 132, a smart hat (not shown), or other smart wearable device, e.g., where the term smart may, for example, indicate that the wearable device includes some type of logic or circuitry, such as a processing circuitry (e.g., a processor), memory for storing information, a wireless interface, and/or other circuitry or logic, for example. These are merely some example wearable devices, and others may be used or provided.

Figure 2:
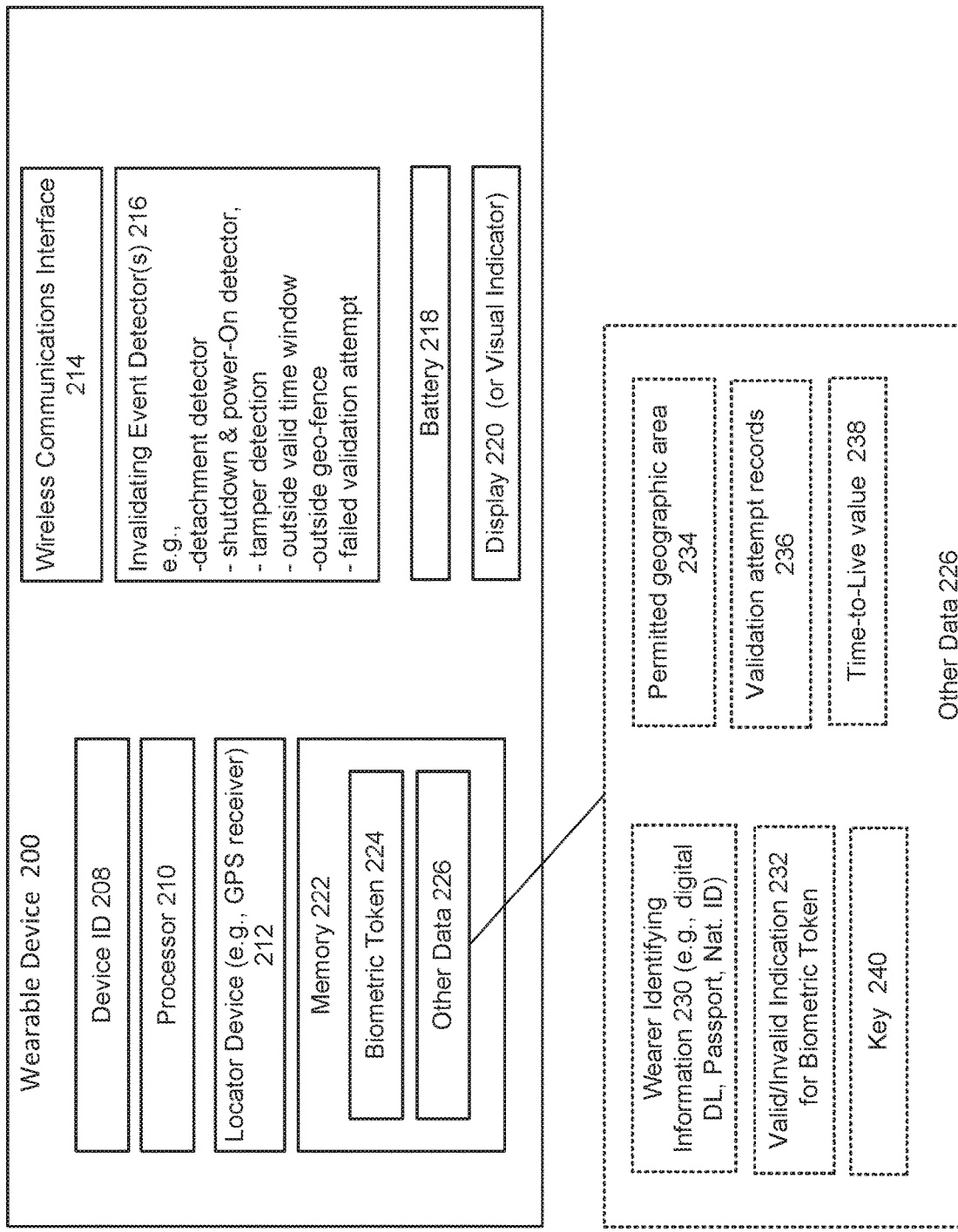
FIG. 2 is a diagram illustrating a wearable device according to an example embodiment.

FIG. 2 is a diagram illustrating a wearable device according to an example embodiment. For example, wearable device 200 may include a device identifier (device ID) 208 that serves to identify the wearable device, such as, e.g., a globally unique and immutable device identifier that can be read from the device by the appropriate type of reader (e.g., a camera for a QR code, an NFC terminal for an RFID chip).

Wearable device 200 may also include a processing circuitry (e.g., such as processor 210), a locator device 212 (e.g., a Global Positioning System (GPS) receiver) to determine the location of the wearable device, a memory 222 that may store a biometric token 224 and other data 226. Wearable device 200 may also include a wireless communications interface 214 for communicating via wireless communications with a computer, a terminal, a server, etc. Wireless communications interface 214 may be, for example, a near field communications (NFC) interface, a Bluetooth interface, a wireless local area network (WLAN) or WiFi interface, a LTE interface or 5G wireless interface, or other wireless interface. Wearable device 200 may also include a battery 218 for providing power to the circuitry of the wearable device, and a display 220 (or other visual indicator) that may display information, such as a valid/invalid status of the biometric token 224 on the wearable device 200.

Wearable device 200 may also include invalidating event detector(s) 216, which may include one or more detectors for detecting or determining an invalidating event that may invalidate (or render invalid) the biometric token 224, e.g., according to a policy for use of the wearable device. In an illustrative embodiment, an invalidating event detector 216 may include a detachment detector to detect a detachment of the wearable device 200 from a wearer 100 of the device. For example, a pressure sensor may detect a change in pressure in proximity to the user's finger or wrist (e.g., a decrease in pressure may indicate detachment of the wearable device), a temperature sensor that may detect a drop in temperature when the wearable device is removed or detached from the wearer, a pulse detector that may detect a presence of a pulse when the device is attached and an absence of a pulse as the invalidating event.

Other types of invalidation event detectors 216 may be used as well. A shutdown and/or power-on detector may detect when the circuitry for the wearable device is shut down and/or powered back on. Thus, for example, a power-on detector may detect that the wearable device is powered on or booted up, etc., which may be considered an invalidating event (e.g., because the wearable device may have been detached from the original wearer and then re-attached to a different person/wearer when the wearable device was powered off/powered down). A tamper detector may detect one or more types of tampering with the device, e.g., such as removal of a battery plate, removal of a battery, altering a display, severing or breaking of a wrist band or other portion of the wearable device, etc. A valid time window detector may determine if the biometric token 224 is expired with respect to the valid time window or valid time to live value for such biometric token (e.g., the biometric token 224 is invalid after the valid time window or after the time to live (TTL) expires). A geographic fence detector may detect that the wearable device 200 (or the locator device 212) is or has traveled to a location that is outside of a permitted geographical area for the wearable device 200 or the biometric token 224. Also, in some cases, a failed validation attempt of the biometric token (where a terminal or computer attempted but was unable to validate the biometric token 224) may be detected and may be considered an invalidating event. Invalidating event detector 216 may detect other types of invalidating events.

Also, as shown in FIG. 2, memory 222 may include other data 226. For example, all or part of data 226 may be stored either as part of the biometric token 224, or alternatively may be stored in memory 222 separately from the biometric token 224. Data 226 may include, for example, wearer identifying information 230, which may include digital or electronic documents for identification that may be associated with or may identify the wearer, such as a driver's license, a Passport, a VISA, a national identification card (National ID card), etc.

Data 226 may include a valid/invalid indication 232 that indicates whether the biometric token 224 is valid or invalid. For example, the valid/invalid indication is marked by processor 210 as invalid when an invalidating event is detected. Data 226 may also include a permitted geographic area 234 for the biometric token, the wearer or the wearable device. Thus, for example, the processor 210 may check a location of the wearable device 200 (based on a location indicated by locator device 212), and compare the location of the wearable device to the permitted geographic area 234 (e.g., a presence of the wearable device 200 outside of the permitted geographic area may be an invalidating event).

Data 226 may also include a time to live value 238 (or valid time window) that may indicate a time period for which the biometric token is valid. Processor 210 may read the time to live value (or compare a current time to a valid time window), to determine whether the biometric token 224 is still valid. Thus, an invalidating event for the biometric token 224 may occur when the time is outside of the valid time window, or the time to live value 238 has expired.

Data 226 may also include validation attempt records 236, which may record information associated with one or more attempts (which may be successful or unsuccessful) to validate the biometric token 224, e.g., such as a time of a validation attempt, information identifying an application, a computer and/or an authorized officer that performed the validation attempt on the biometric token, and/or a result of the validation attempt (e.g., either validated, or not validated).

Data 226 may also include a key 240 that may be used to encrypt the biometric token 224 before the biometric token is stored in memory, and/or to decrypt the biometric token 224 when an authorized computer or terminal is reading the biometric token 224.

Figure 3:
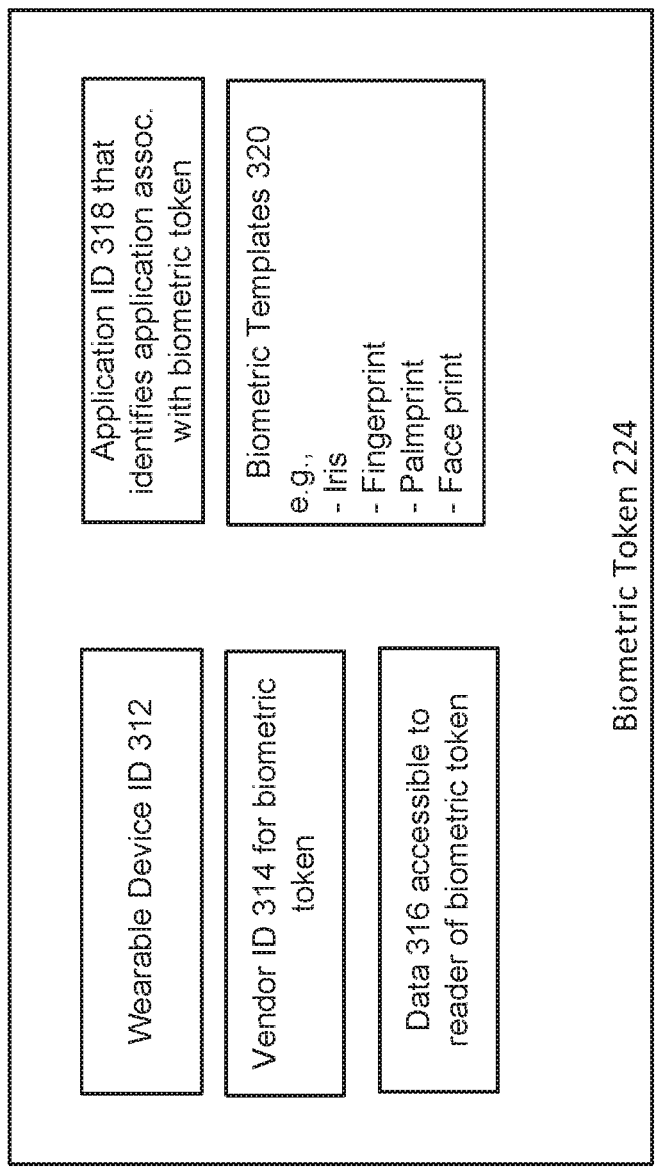
FIG. 3 is a diagram illustrating a biometric token according to an example embodiment.

FIG. 3 is a diagram illustrating a biometric token according to an example embodiment. Biometric token 224 may include, for example, data that may be used to determine if the wearable device (or the biometric token 224), in its current state, is valid or invalid for a particular use. Thus, for example, a biometric token 224 may include: a wearable device identifier (wearable device ID) 312 that may uniquely identify the wearable device that the biometric token 224 is generated or provided for; a vendor identifier (vendor ID) 314 that uniquely identifies the vendor who generated the biometric token 224; an application identifier (application ID) 318 that, for a vendor ID, uniquely identifies the application this biometric token 224 is associated with. Biometric token 224 may include one or more biometric templates 320 (e.g., a fingerprint template from a fingerprint scan, a face template from a face scan, an iris template from an iris scan, . . . ), which can be compared with new templates generated from wearer biometrics to determine similarity. A biometric template may be a digital reference of distinct characteristics that have been extracted from a biometric sample or biometric scan. Biometric templates may be used during a biometric authentication process, e.g., by comparing a stored biometric template to a biometric template generated from a biometric scan of the wearer, to confirm similarity between the two biometric templates. Also, biometric token 224 may also include data 316 which is accessible to the reader of the biometric token (e.g., which may require a key to decrypt the biometric token and associated data, for example). Data 316 may include, for example, all or part of other data 226. As noted, a key 240 (FIG. 2) may be associated with the biometric token 224, e.g., an may be used to encrypt the biometric token to be stored in memory 222 and/or decrypt the biometric token 224 that is ready from memory 22 and then allow access to or read any data (e.g., data 226 or data 316) associated with the biometric token 224, for example.

According to an example embodiment, a biometric token may include a hardware token and a software token.

1) A hardware token:
may use a unique ID (e.g., device ID 208, FIG. 2) assigned by a vendor or manufacturer when they build hardware, such as the wearable device or the electronics of the wearable device, e.g., similar to a MAC Address on a network card.

Each wearable device may generate a hardware token by using the unique ID (Real Hardware unique ID, such as device ID 208) for hardware.

Another unique ID (Virtual unique ID) for hardware may be assigned as well, which may be referenced by other tokens for software.

The virtual unique ID can be just one ID for each device or it can be more than one virtual ID per device. The virtual ID generated by software, it could be shared between different application or blocking by security.

An API (application programming interface) may be used to obtain or read the virtual unique ID for hardware and to get related information such as token expired history.

A software token may be generated by referencing the virtual ID and software vendor ID.

Example)
1) Virtual ID: D7F69747-ED5B-48C1-81AB-A57D69D33437
2) Vendor ID: 0FBF14B9-EA13-4AC0-B28F-32CB1771B826

Software token may have various types of data such as document image, fingerprint, iris, banking information, schedule, memo, and etc.

Software token may be provided to manage mostly biometric and identity related information such a face, fingerprint, iris, passport, driver's license, and etc.

All other 3$^{rd}$ party software can reference data by relationship. Or, all other 3$^{rd}$ party software may reference data by security level association based on an agreement between vendor or parties as to how data can be shared, and what data can be shared or accessed.

Biometric data, such as user documents or wearer identifying information (e.g., drivers license/DL, passport, VISA), and a biometric pattern for Fingerprint, Iris scan, etc.—this data may be accessed (decrypted and read) based on the key that is stored on the wearable device.

Examples of a shared key 240, that may be used (note, in this example that a first shared key may be used to verify biometric data and wearer identifying information, while a second shared key may be used to update biometrics or biometric patterns stored in wearable device and update in memory the identity or stored wearer identifying information:

A) Shared key: 13E011B7-17E3-438A-BAD6-A0A0D529B961
  1) Fingerprint of wearer can be verified (e.g., fingerprint template may be read from memory based on shared key, and compared to a fingerprint generated based on fingerprint scan of wearer, to confirm same or similar patterns
  2) Iris can be verified
  3) Identity can be verified (e.g., by comparing digital image of
B) Shared key: 9F9D2E3E-AAE5-4D63-8C09-312BFD0AEFFF
  1) Fingerprint can be updated
  2) Iris can be updated
  3) Identity can be updated.

Below is an illustrative example of a token and a key:

Token    eyJ0eXAiOiJKV1QiLCJhbGciOiJIUzI1NiJ9.eyJzdWIiOiIx
MjM0NTY3ODkwIiwibmFtZSI6IkpvaG4gRG9lIiwiYWRta
W4iOnRydWUsImp0aSI6IjZjZDU0MDBjLTFmZjMtNGU5

-continued

| | |
|---|---|
| | Mi05MDMwLTE5NDhlMTYzMjU0ZCIsImlhdCI6MTUy<br>MjIzODA4OSwiZXhwIjoxNTIyMjQxNjg5fQ._JWbo<br>ElEE17e2q6NBfLExde64hvlkEq5f788Aj_qSU0 |
| Header | {<br>"typ": "JWT",<br>"alg": "HS256"<br>} |
| Payload | {<br>"sub": "1234567890",<br>"name": "John Doe",<br>"admin": true,<br>"jti": "6cd5400c-1ff3-4e92-9030-1948e163254d",<br>"iat": 1522238089,<br>"exp": 1522241689<br>} |
| Signing Key | secret |

The above example is using "secret" as a key. The header shows a type of token and type of encryption, payload can be any data that may be read based on decryption using the key.

Figure 4:
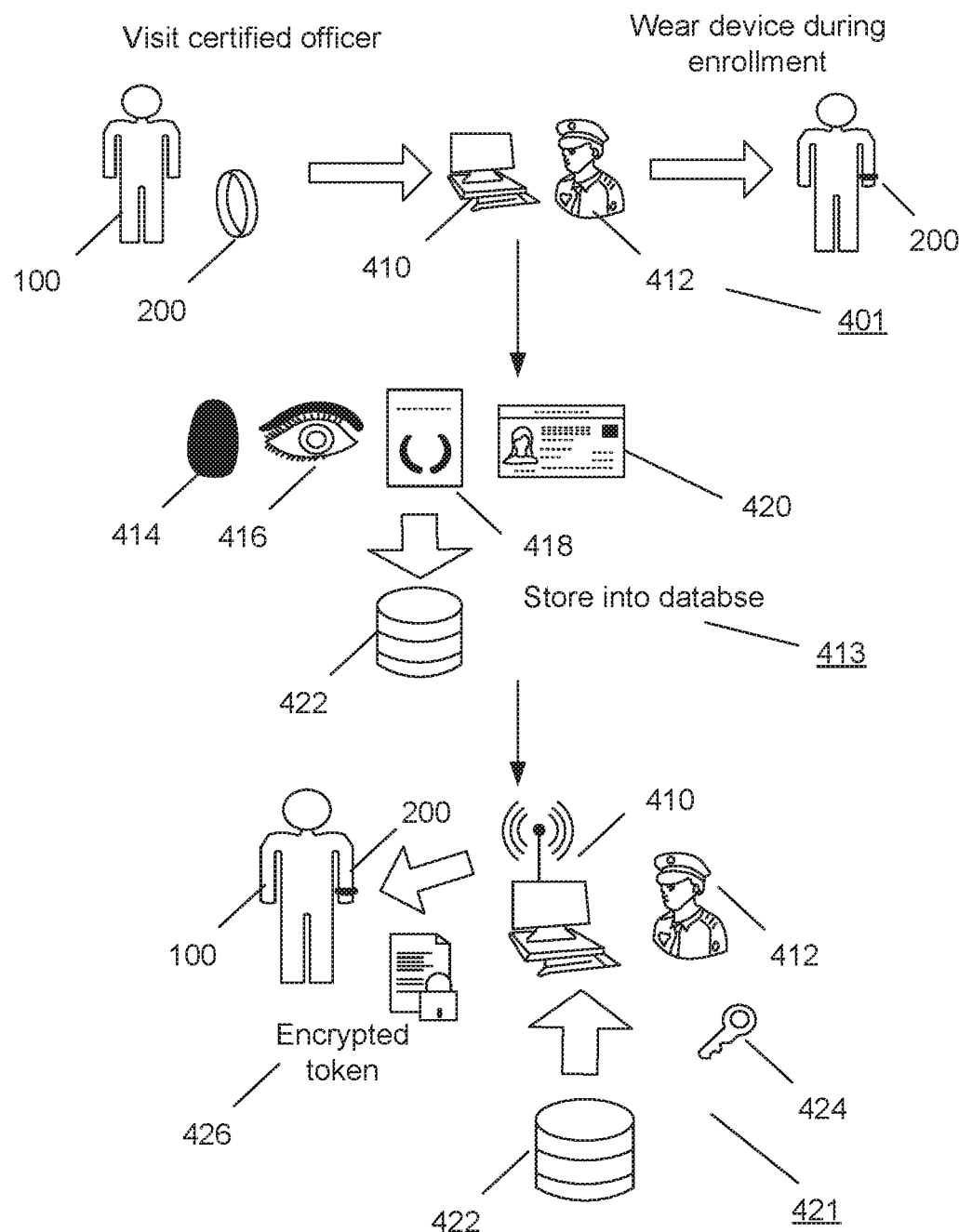
FIG. 4 is a diagram illustrating enrollment according to an example embodiment.

FIG. 4 is a diagram illustrating enrollment according to an example embodiment. Enrollment may allow association of the wearable device 200 to a vendor's systems, and establishes (e.g., generates, encrypts and stores) the biometric token 224 on the wearable device 200. An Enrollment Station, which permits the association of the wearable device 200 to a vendor's systems, and establishes the biometric token on the wearable device. According to an example embodiment, the enrollment station, may provide a biometric token 224 on the wearable device.

According to an example embodiment, a computer 410 that may be used for enrollment, or an enrollment station, may include, for example: 1. A set of information to be stored on the wearable device, including the vendor identifier (vendor ID) 314, the Application Identifier (application ID) 318, and data (e.g., 316 and/or 226); 2. A processor, memory and a communications interface that allows communication with the wearable device's communications interface; 3. One or more biometric reader components, such as a fingerprint scanner or iris scanner, palm print scanner, a face scanner, etc., that collects wearer biometrics (wearer biometric scans or information) and generates biometric templates for each biometric mode that is scanned or read; 4. A biometric token generator, which generates or creates a biometric token 224 for storage on a wearable device 200 using the biometric templates, the device ID, the vendor ID, the application ID and/or the data.

As shown in FIG. 4, the enrollment process will be briefly described. As shown in FIG. 4, at 401, a wearer 100 visits a certified officer 412, who has a computer 410. A wearer 100 wears the wearable device 200 during enrollment. At 413, the officer 412 may use biometric readers on the enrollment workstation (computer 410) to read biometric information from the wearer, e.g., take iris scans 416, a fingerprint scan 414, palm print scan, or other biometric information from the wearer 100. The enrollment station or computer 410 may generate biometric patterns for each of the biometric information of the wearer. Also, the wearer's documents or identifying information are collected and scanned, e.g., a passport 418 and a driver's license 40, for example. The biometric patterns and wearer identifying information are stored in a database 422. Also, various identification information for the wearable device is collected and stored in database 422, e.g., wearable device ID 312, vendor ID 314, application ID 318, and possibly data 226 or 316. At 421, the enrollment workstation or computer 410 generates a biometric token from the stored information in database 422. A key 424 may be used to encrypt the biometric token to generate an encrypted biometric token 426, which is stored on the wearable device 200 by the computer 410 or enrollment workstation.

Figure 5:
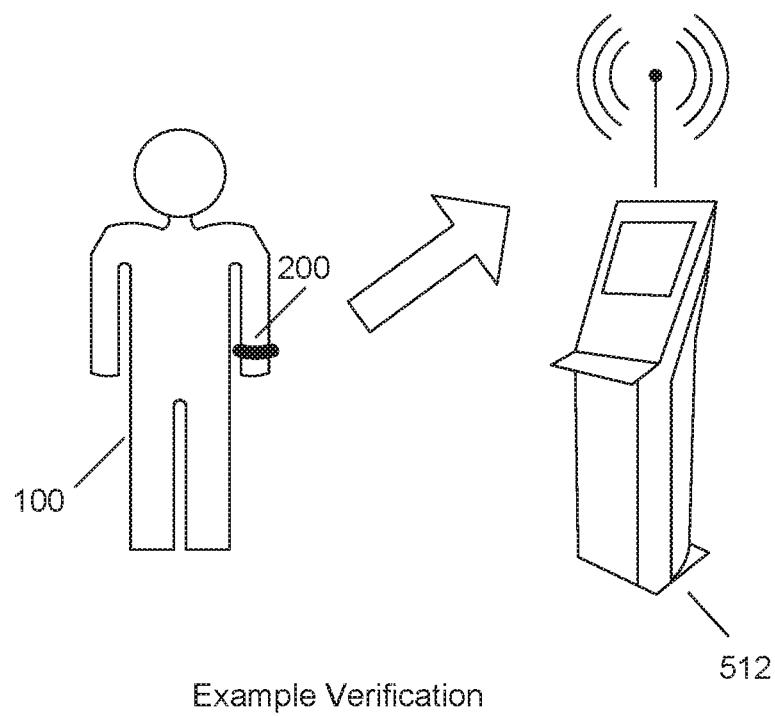
FIG. 5 is a diagram illustrating verification according to an example embodiment.

FIG. 5 is a diagram illustrating verification according to an example embodiment. A Verification Station may permit the reading and verification of the biometric token 224 that is stored on a wearable device. A verification station (or a computer 512) used for verification, may include the following, by way of example: 1) a processor, memory and wireless communications interface to communicate with the wearable device; 2. A biometric token validator, which can check the biometric token for validity; 3. A biometric token reader, which can decrypt (based on the key) the token and retrieve information from the biometric token, such as the biometric templates and/or wearer identifying information, the device ID 312, the vendor ID 314, the application ID 318, and data 316 and/or 226.

Verification of the wearable device and/or biometric token may include the following by way of example. 1) A wearer 100 is wearing the wearable device 200 with a biometric token 224 stored thereon; 2. wearer presents the wearable device and establishes communication to the verification station 512; 3. Verification station uses biometric token reader to retrieve biometric token and other data (such as timestamps of removals or geo-fence exits) from wearable device 200; 4. verification station 512 uses biometric token validator to ensure token is present and still valid—that no invalidation events have occurred since activation and that the token's time-to-live has not expired. Thus, for example, as part of verification, the verification station 512 may read and check the valid/invalid indication (or status flag) 232 within the biometric token 224 to confirm that the biometric token is still indicated as valid; 5. verification station 512 reports validation/verification attempt and results to the attached system(s) for action (e.g. unlock hotel room door, show officer that passenger is allowed to board, show attendant that park attendee can get on ride, provide wearer with access to building, or allow wearer access to secured computer devices, . . . ). Also, the verification station 512 may update the validation or verification attempt records 236 to include information related to this verification or validation attempt (e.g., time of verification, application ID of application that performed verification, verification result (valid or invalid), etc. These updated verification attempt records may be stored or written back to memory 222 of the wearable device within validation/verification attempt records 236, for example. Note, that verification of the biometric token does not require the wearer presenting his/her wearer identifying documents and/or rescanning the wearer's biometrics. Rather, the verification station 512 may read the biometric token from the wearable device, and then determine (e.g., based on valid/invalid indication) whether or not the biometric token 224 is valid. Thus, validation or verification of a wearer may be faster, more reliable, and not require input or providing of biometrics or wearer identifying information at the verification station.

As described, the invalidating event detector(s) 216 (FIG. 2) may detect one or more invalidating events, which may render the biometric token invalid, including the following example invalidating events:

Expire Biometric Tokens based on events and policies
    internally, such as:
Attachment and Detachment;
Shutdown and Power On;

Tampering;
Expire based on time;
Expire based on failed Validation attempts; and
Entering or leaving a Geofence.

As noted herein, a number of invalidating events may have caused the biometric token to become (or be indicated as) invalid. Reactivation or revalidation may be used to reactivate (and mark as valid) the biometric token in a wearable device. This may include for example: 1. Wearer is wearing the wearable device with a biometric token in memory or storage; 2. Wearer presents wearable device at enrollment station; 3. Operator uses biometric readers on the enrollment workstation to read biometric information (e.g., to obtain iris scan, fingerprint scan face scan, palm print scan, etc.), and calculate biometric patterns based on these biometric scans of the wearer; 4. Enrollment station compares biometric templates stored in biometric token of wearable device to those collected from the wearer (they should be a minimum threshold of similarity in pattern, to be a match, and thus validating the biometric token or wearable device). 5. If they match (at least a minimum threshold of pattern matching), reactivate the biometric token and store time of activation in memory. Thus, the (e.g., updated) biometric token may be stored again in memory of the wearable device, or at least the valid/invalid indication 232 in memory of the wearable device may be changed to valid, and validation attempt records 236 may be updated with information or records of this revalidation or reverification.

According to some illustrative examples, verification may be performed at an airport (e.g., to allow the wearer to board the plane), an office building (to provide the wearer with access to the building), a train station, etc. By using the wearable device with the biometric token, where the information (e.g., valid/invalid indication) on the wearable device may indicate whether or not the biometric token is valid (e.g., based on use of invalidation event detector(s)). According to an example embodiment, if the biometric token is valid, then trust is established that the wearer is associated with (e.g., identified by) the biometric information and wearer identifying information stored on the wearable device. Thus, in this manner, the wearable device with a valid biometric token, which has not violated the policy that manages use of the wearable device (e.g., wearable device has not been detached or tampered with), reliably indicates the identity of the wearer and/or establishes a trust that wearer identifying information (e.g., DL, passport, VISA, national ID card, . . . ), linked to the biometric token, is associated with (e.g., identifies) the wearer of the wearable device. The wearer identifying information, linked to or associated with the biometric token, may be stored within a database (e.g., 422). Also, at least in some cases, some or all of the wearer identifying information may also be stored in the memory of the wearable device.

For example, any wearable device (watch, ring, bracelet) containing an indication that the biometric token is valid, such as a certification symbol (e.g., ICAO RFID) that, by using a certified application, employs a trusted biometric token. The biometric token is more reliable because it is based on multiple biometric information such as fingerprints, Iris, and/or Facial images (or patterns thereof), and wearer identifying information is linked to or associated with the biometric token. Reliability is also improved through the use of invalidation event detectors to ensure that the biometric token is still valid (e.g., wearable device not detached, not tampered with, not expired, . . . ). This identifying information (e.g., Passport, Visa, driver's license) may be exported to (and stored on) the wearable device. This wearable device can be accessed via a wireless, e.g., NFC (Near Field Communication), reader such as an RFID reader. For example, at a verification station, the wearer can be trusted without using a Passport, Visa, driver's license, etc., because it is token based (and based on multiple biometrics), and it is marked or indicated as valid. The device can be renewed or revalidated by personnel, (e.g., Immigration Officer) using a certified application.

Example 1

Figure 6:
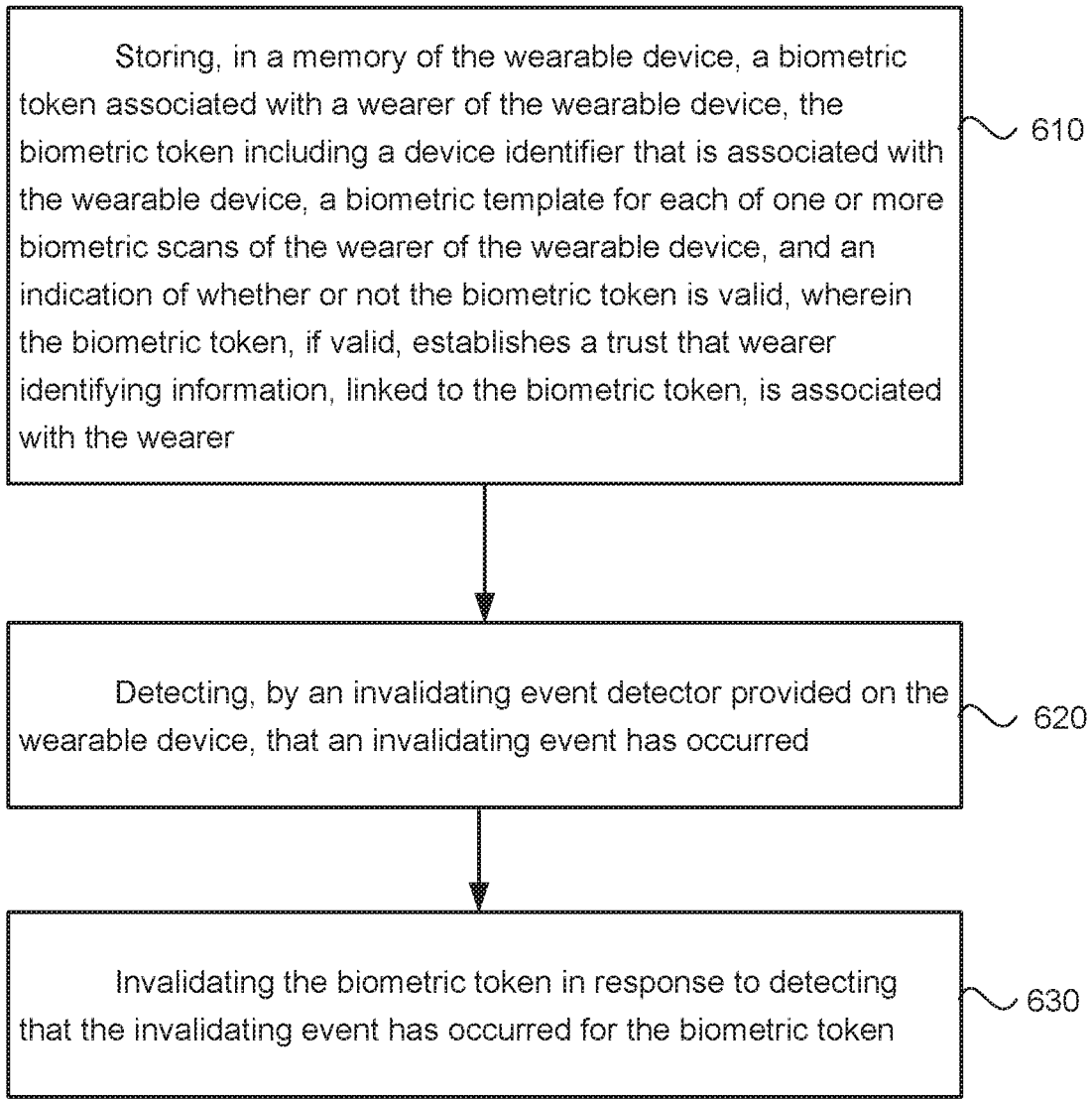
FIG. 6 is a flow chart illustrating a method of managing a biometric token that is provided on a wearable device according to an example embodiment.

FIG. 6 is a flow chart illustrating a method of managing a biometric token that is provided on a wearable device according to an example embodiment. Operation 610 includes storing, in a memory of the wearable device, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer. Operation 620 includes detecting, by an invalidating event detector provided on the wearable device, that an invalidating event has occurred. And, operation 630 includes invalidating the biometric token in response to detecting that the invalidating event has occurred for the biometric token.

Example 2

The method of example 1 wherein the detecting that an invalidating event has occurred comprises detecting one or more of the following invalidating events: that a time-to-live for the biometric token has expired; that a location of the wearable device has traveled to or been located at a location that is outside of a permitted geographic area for the biometric token; and that the wearable device has become detached from the wearer.

Example 3

The method of any of examples 1-2 wherein the detecting that an invalidating event has occurred comprises: determining a location of the wearable device; comparing a location of the wearable device to a permitted geographic area associated with the wearer or the biometric token; detecting that the location of the wearable device is outside of the permitted geographic area; and invalidating the biometric token in response to detecting that the location of the wearable device was outside of the permitted geographic region.

Example 4

The method of any of examples 1-3, wherein the invalidating the biometric token comprises performing at least one of the following in response to detecting that an invalidating event has occurred for the biometric token: storing information in the memory indicating that the biometric token is invalid; and deleting from the memory, or modifying within the memory, at least a portion of the biometric token so as to render to biometric token invalid.

Example 5

The method of any of examples 1-4 wherein the wearer identifying information comprises a digital version of at least one of: a drivers license of the wearer of the wearable device; a national ID card of the wearer of the wearable device; a ticket or pass assigned to the wearer of the wearable device; a passport of the wearer of the wearable device; and a VISA of the wearer of the wearable device.

Example 6

The method of any of examples 1-5 and further comprising: updating a status of the biometric token from valid to invalid if the detachment sensor detects that the wearable device was detached from the wearer.

Example 7

The method of any of examples 1-6 and further comprising storing in memory one or more of the following for one or more validation attempts based on the biometric token stored in the memory of the wearable device: information indicating that a validation attempt was performed for the biometric token; a time of the validation attempt; information identifying an application that performed the validation attempt; and a result of the validation attempt.

Example 8

The method of any of examples 1-7 and further comprising performing at least one of the following in response to detecting an invalidating event: storing information in the memory indicating a time that the invalidating event was detected; and storing in the memory an identification of the invalidating event.

Example 9

A non-transitory computer readable medium storing executable instructions that when executed by at least one processor is configured to perform the method of any of examples 1-8.

Example 10

An apparatus comprising means for performing the method of any of examples 1-8.

Example 11

A wearable device that is configured to store a biometric token associated with a wearer of the wearable device, the wearable device comprising: a wireless communications interface; a processing circuitry; a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; an invalidating event detector configured to determine if an invalidating event has occurred; wherein the processing circuitry is configured to invalidate the biometric token in response to detecting that an invalidating event has occurred for the biometric token.

Example 12

The wearable device of example 11, wherein the invalidating event detector is configured to determine an occurrence of one or more invalidating events for the biometric token, including being configured to detect one or more of the following invalidating events of: that a time-to-live for the biometric token has expired; that a location of the wearable device has travelled to or been located at a location that is outside of a permitted geographic area for the biometric token; and that the wearable device has become detached from the wearer.

Example 13

The wearable device of any of examples 11-12, wherein the invalidating event detector comprises a detachment sensor that is configured to detect if the wearable device becomes detached from the wearer; and wherein the processing circuitry is configured to invalidate the biometric token in response to detecting that the wearable device was detached from the wearer.

Example 14

The wearable device of any of examples 11-13, wherein the invalidating event detector comprises a location detector configured to determine a location of the wearable device; wherein the processing circuitry is configured to: compare a location of the wearable device to a permitted geographic area associated with the wearer or the biometric token; detect that the location of the wearable device is outside of the permitted geographic area; and invalidate the biometric token in response to detecting that the location of the wearable device was outside of the permitted geographic region.

Example 15

The wearable device of any of examples 11-14, wherein the processing circuitry being configured to invalidate the biometric token comprises the processing circuitry configured to perform at least one of the following in response to detecting that an invalidating event has occurred for the biometric token: store information in the memory indicating that the biometric token is invalid; and delete, from the memory, at least a portion of the biometric token so as to render to biometric token invalid.

Example 16

The wearable device of any of examples 11-15, wherein the wearer identifying information is stored in the memory.

Example 17

The wearable device of any of examples 11-16, wherein the processing circuitry comprises a processor.

Example 18

The wearable device of any of examples 11-17, wherein the wearer identifying information comprises a digital version of at least one of: a drivers license of the wearer of the wearable device; a national ID card of the wearer of the wearable device; a ticket or pass assigned to the wearer of the wearable device; a passport of the wearer of the wearable device; and a VISA of the wearer of the wearable device.

Example 19

The wearable device of any of examples 11-18, wherein the wearable device further comprises a visual indicator that indicates whether the biometric token stored on the wearable device is valid or invalid.

Example 20

The wearable device of any of examples 11-19, wherein the wearable device comprises at least one of: a ring; a bracelet; a watch; a necklace; and a belt.

Example 21

The wearable device of any of examples 11-20, wherein the processing circuitry is configured to update a status of the biometric token from valid to invalid if the detachment sensor detects that the wearable device was detached from the wearer.

Example 22

The wearable device of any of examples 11-21, wherein the processing circuitry is further configured to store in memory one or more of the following for one or more validation attempts based on the biometric token stored in the memory of the wearable device: information indicating that a validation attempt was performed for the biometric token; a time of the validation attempt; information identifying an application that performed the validation attempt; and a result of the validation attempt.

Example 23

The wearable device of any of examples 11-22, wherein the processing circuitry is configured to further perform at least one of the following in response to detecting an invalidating event: store information in the memory indicating a time that the invalidating event was detected; and store in the memory an identification of the invalidating event.

Example 24

A wearable device that is configured to store a biometric token associated with a wearer of the wearable device, the wearable device comprising: a wireless communications interface; a processing circuitry; a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; a detachment sensor that is configured to detect if the wearable device becomes detached from the wearer; wherein the processing circuitry is configured to invalidate the biometric token in response to detecting that the wearable device was detached from the wearer.

Example 25

The wearable device of example 24, wherein the processing circuitry being configured to invalidate the biometric token comprises the processing circuitry configured to perform at least one of the following in response to detecting that the wearable device was detached from the wearer: store information in the memory indicating that the biometric token is invalid; and delete, from the memory, at least a portion of the biometric token so as to render to biometric token invalid.

Example 26

The wearable device of any of examples 24-25, wherein the processing circuitry comprises a processor.

Example 27

The wearable device of any of examples 24-26, wherein the wearer identifying information comprises a digital version of at least one of: a drivers license of the wearer of the wearable device; a national ID card of the wearer of the wearable device; a ticket or pass assigned to the wearer of the wearable device; a passport of the wearer of the wearable device; and a travel authorization document, such as a VISA of the wearer of the wearable device.

Example 28

The wearable device of any of examples 24-27 wherein at least a portion of the wearer identifying information is stored in the memory of the wearable device.

Example 29

The wearable device of any of examples 24-28 wherein the biometric token associated with a wearer of the wearable device, when valid, establishes trust that the wearer identifying information linked to the biometric token is associated with and identifies the wearer of the wearable device; and wherein the biometric token associated with a wearer of the wearable device, when invalid, does not establish trust that the wearer identifying information linked to the biometric token is associated with or identifies the wearer of the wearable device.

Example 30

The wearable device of any of examples 24-29 wherein the biometric token associated with a wearer of the wearable device, when valid, establishes trust that the wearer identifying information linked to the biometric token identifies the wearer of the wearable device, without requiring the wearer to separately provide the identifying information and/or without requiring one or more biometric scans to be performed on the wearer to confirm identity of the wearer.

Example 31

The wearable device of any of examples 24-30, wherein the wearable device further comprises a visual indicator that indicates whether the biometric token stored on the wearable device is valid or invalid.

Example 32

The wearable device of any of examples 24-31, wherein the wearable device comprises at least one of: a ring; a bracelet; a watch; a necklace; and a belt.

Example 33

The wearable device of any of examples 24-32 wherein the wearable device is configured to update a status of the biometric token from valid to invalid if the detachment sensor detects that the wearable device was detached from the wearer.

Example 34

The wearable device of any of examples 24-33 wherein the processing circuitry is further configured to store in memory one or more of the following for one or more validation attempts based on the biometric token stored in the memory of the wearable device: information indicating that the validation attempt was performed for the biometric token; a time of the validation attempt; information identifying an application that performed the validation attempt; and a result of the validation attempt.

Example 35

A wearable device that is configured to store a biometric token associated with a wearer of the wearable device, the wearable device comprising: a wireless communications interface; a processing circuitry; a memory configured to store information indicating a permitted geographic area associated with the wearer, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer; a location detector configured to determine a location of the wearable device; wherein the processing circuitry is configured to: compare a location of the wearable device to the permitted geographic area associated with the wearer; detect that the location of the wearable device is outside of the permitted geographic area associated with the wearer; and invalidate the biometric token in response to detecting that the location of the wearable device was outside of the permitted geographic region.

Example 36

The wearable device of example 35, wherein the processing circuitry being configured to invalidate the biometric token comprises the processing circuitry configured to perform at least one of the following in response to detecting that the location of the wearable device was outside of the permitted geographic area: store information in the memory indicating that the biometric token is invalid; and delete, from the memory, at least a portion of the biometric token so as to render to biometric token invalid.

Example 37

The wearable device of any of examples 35-36 wherein the processing circuitry is further configured to: store information indicating that a reason for the token being invalid is the wearable device being detected outside of the permitted geographic region; and store information in the memory indicating a time that the location of the wearable device was determined as being outside of the permitted geographic area.

Thus, various implementations of the systems and techniques described here can be realized in digital electronic circuitry, integrated circuitry, specially designed ASICs (application specific integrated circuits), FPGAs (field-programmable gate arrays), computer hardware, firmware, software, and/or combinations thereof. For example, a FPGA may be considered as a software programmed circuit, and an ASIC may be considered a hardware programmed circuit. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedure and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It will be appreciated that the above embodiments that have been described in particular detail are merely example or possible embodiments, and that there are many other combinations, additions, or alternatives that may be included.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

What is claimed is:

1. A wearable device that is configured to store a biometric token associated with a wearer of the wearable device, the wearable device comprising:
    a wireless communications interface;
    a processing circuitry;
    a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer;
    an invalidating event detector configured to determine if an invalidating event has occurred;
    the invalidating event detector including at least a power-on detector to detect an invalidating event based on detecting that the wearable device has been powered on or booted up;
    wherein the processing circuitry is configured to:
        invalidate the biometric token in response to detecting that an invalidating event has occurred for the biometric token; and
        store, in the memory of the wearable device, information associated with the invalidating event.

2. The apparatus of claim 1, wherein the invalidating event detector is configured to determine an occurrence of one or more invalidating events for the biometric token, including being further configured to detect one or more of the following invalidating events of:
    that a time-to-live for the biometric token has expired;
    that a location of the wearable device has traveled to or been located at a location that is outside of a permitted geographic area for the biometric token; and
    that the wearable device has become detached from the wearer.

3. The apparatus of claim 1:
    wherein the invalidating event detector comprises a detachment sensor that is configured to detect if the wearable device becomes detached from the wearer; and
    wherein the processing circuitry is configured to invalidate the biometric token in response to detecting that the wearable device was detached from the wearer.

4. The apparatus of claim 1:
    wherein the invalidating event detector comprises a location detector configured to determine a location of the wearable device;
    wherein the processing circuitry is configured to:
        compare a location of the wearable device to a permitted geographic area associated with the wearer or the biometric token;
        detect that the location of the wearable device is outside of the permitted geographic area; and
        invalidate the biometric token in response to detecting that the location of the wearable device was outside of the permitted geographic region.

5. The wearable device of claim 1 wherein the processing circuitry being configured to invalidate the biometric token comprises the processing circuitry configured to perform at least one of the following in response to detecting that an invalidating event has occurred for the biometric token:
    store information in the memory indicating that the biometric token is invalid; and
    delete from the memory, or modify within the memory, at least a portion of the biometric token so as to render to biometric token invalid.

6. The wearable device of claim 1 wherein the wearer identifying information is stored in the memory.

7. The wearable device of claim 1 wherein the wearer identifying information comprises a digital version of at least one of:
    a drivers license of the wearer of the wearable device;
    a national ID card of the wearer of the wearable device;
    a ticket or pass assigned to the wearer of the wearable device;
    a passport of the wearer of the wearable device; and
    a VISA of the wearer of the wearable device.

8. The wearable device of claim 1, wherein the wearable device further comprises a visual indicator that indicates whether the biometric token stored on the wearable device is valid or invalid.

9. The wearable device of claim 1, wherein the wearable device comprises at least one of:
    a ring;
    a bracelet;
    a watch;
    a necklace; and
    a belt.

10. The apparatus of claim 1 wherein the processing circuitry is configured to update a status of the biometric token from valid to invalid if the detachment sensor detects that the wearable device was detached from the wearer.

11. The wearable device of claim 10, wherein the processing circuitry is further configured to store in memory one or more of the following for one or more validation attempts based on the biometric token stored in the memory of the wearable device:
    information indicating that a validation attempt was performed for the biometric token;
    a time of the validation attempt;
    information identifying an application that performed the validation attempt; and
    a result of the validation attempt.

12. The wearable device of claim 1 wherein the processing circuitry being configured to store, in the memory of the wearable device, information associated with the invalidating event comprises the processing circuitry being configured to:
    store information in the memory indicating a time that the invalidating event was detected; and
    store in the memory an identification of the invalidating event.

13. A method of managing a biometric token that is provided on a wearable device, the method comprising:
    storing, in a memory of the wearable device, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer;
    detecting, by an invalidating event detector provided on the wearable device, that an invalidating event has occurred, including detecting, by a power-on detector, that the wearable device has been powered on or booted up;
    invalidating the biometric token in response to detecting that the invalidating event has occurred for the biometric token; and
    storing, in the memory of the wearable device, information associated with the invalidating event.

14. The method of claim 13 wherein the detecting that an invalidating event has occurred further comprises detecting one or more of the following invalidating events:
    that a time-to-live for the biometric token has expired;
    that a location of the wearable device has traveled to or been located at a location that is outside of a permitted geographic area for the biometric token; and
    that the wearable device has become detached from the wearer.

15. The method of claim 13, wherein the detecting that an invalidating event has occurred further comprises:
    determining a location of the wearable device;
    comparing a location of the wearable device to a permitted geographic area associated with the wearer or the biometric token;
    detecting that the location of the wearable device is outside of the permitted geographic area; and
    invalidating the biometric token in response to detecting that the location of the wearable device was outside of the permitted geographic region.

16. The method of claim 13, wherein the invalidating the biometric token comprises performing at least one of the following in response to detecting that an invalidating event has occurred for the biometric token:
    storing information in the memory indicating that the biometric token is invalid; and
    deleting, from the memory, at least a portion of the biometric token so as to render to biometric token invalid.

17. The method of claim 13 wherein the wearer identifying information comprises a digital version of at least one of:
    a drivers license of the wearer of the wearable device;
    a national ID card of the wearer of the wearable device;
    a ticket or pass assigned to the wearer of the wearable device;
    a passport of the wearer of the wearable device; and
    a VISA of the wearer of the wearable device.

18. The method of claim 13 and further comprising:
    updating a status of the biometric token from valid to invalid if a detachment sensor detects that the wearable device was detached from the wearer.

19. The method of claim 13 and further comprising storing in memory one or more of the following for one or more validation attempts based on the biometric token stored in the memory of the wearable device:
    information indicating that a validation attempt was performed for the biometric token;
    a time of the validation attempt;
    information identifying an application that performed the validation attempt; and
    a result of the validation attempt.

20. The method of claim 13 wherein the storing, in the memory of the wearable device, information associated with the invalidating event comprises:
    storing information in the memory indicating a time that the invalidating event was detected; and
    storing in the memory an identification of the invalidating event.

21. A wearable device that is configured to store a biometric token associated with a wearer of the wearable device, the wearable device comprising:
    a wireless communications interface;
    a processing circuitry;
    a memory configured to store a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer;
    a detachment sensor that is configured to detect if the wearable device becomes detached from the wearer;
    wherein the processing circuitry is configured to:
        invalidate the biometric token in response to detecting that the wearable device was detached from the wearer; and
        store, in the memory of the wearable device, for one or more validation attempts on the biometric token, a validation attempt record that stores information associated with a validation attempt on the biometric token.

22. The wearable device of claim 21 wherein the processing circuitry being configured to invalidate the biometric token comprises the processing circuitry configured to perform at least one of the following in response to detecting that the wearable device was detached from the wearer:
    store information in the memory indicating that the biometric token is invalid; and
    delete, from the memory, at least a portion of the biometric token so as to render to biometric token invalid.

23. The wearable device of claim 21 wherein the wearer identifying information comprises a digital version of at least one of:
    a drivers license of the wearer of the wearable device;
    a national ID card of the wearer of the wearable device;
    a ticket or-pass assigned to the wearer of the wearable device;
    a passport of the wearer of the wearable device; and a travel authorization document of the wearer of the wearable device.

24. The wearable device of claim 21 wherein at least a portion of the wearer identifying information is stored in the memory of the wearable device.

25. The wearable device of claim 21:
wherein the biometric token associated with a wearer of the wearable device, when valid, establishes trust that the wearer identifying information linked to the biometric token is associated with and identifies the wearer of the wearable device; and
wherein the biometric token associated with a wearer of the wearable device, when invalid, does not establish trust that the wearer identifying information linked to the biometric token is associated with or identifies the wearer of the wearable device.

26. The wearable device of claim 21:
wherein the biometric token associated with a wearer of the wearable device, when valid, establishes trust that the wearer identifying information linked to the biometric token identifies the wearer of the wearable device, without requiring the wearer to separately provide the identifying information and/or without requiring one or more biometric scans to be performed on the wearer to confirm identity of the wearer.

27. The wearable device of claim 21, wherein the wearable device further comprises a visual indicator that indicates whether the biometric token stored on the wearable device is valid or invalid.

28. The wearable device of claim 21, wherein the wearable device comprises at least one of:
a ring;
a bracelet;
a watch;
a necklace; and
a belt.

29. The apparatus of claim 21 wherein the wearable device is configured to update a status of the biometric token from valid to invalid if the detachment sensor detects that the wearable device was detached from the wearer.

30. The wearable device of claim 21, wherein the processing circuitry is further configured to store in memory one or more of the following for one or more validation attempts based on the biometric token stored in the memory of the wearable device:
information indicating that the validation attempt was performed for the biometric token;
a time of the validation attempt;
information identifying an application that performed the validation attempt; and
a result of the validation attempt.

31. The wearable device of claim 21, wherein the validation attempt record stores, in the memory of the wearable device, for one or more validation attempts on the biometric token, a result of the validation attempt to indicate that the biometric token was either validated or not validated.

32. The wearable device of claim 31, wherein the validation attempt record stores, in the memory of the wearable device, for one or more validation attempts on the biometric token, one or more of the following:
a time of the validation attempt;
information identifying an application that performed the validation attempt;
information identifying a computer that performed the validation attempt; or
information identifying an authorized officer that performed the validation attempt.

33. A wearable device that is configured to store a biometric token associated with a wearer of the wearable device, the wearable device comprising:
a wireless communications interface;
a processing circuitry;
a memory configured to store information indicating a permitted geographic area associated with the wearer, a biometric token associated with a wearer of the wearable device, the biometric token including a device identifier that is associated with the wearable device, a biometric template for each of one or more biometric scans of the wearer of the wearable device, and an indication of whether or not the biometric token is valid, wherein the biometric token, if valid, establishes a trust that wearer identifying information, linked to the biometric token, is associated with the wearer;
an invalidating event detector configured to determine if an invalidating event has occurred;
wherein the processing circuitry is configured to:
invalidate the biometric token in response to detecting that an invalidating event has occurred for the biometric token; and
store, in the memory of the wearable device, for one or more validation attempts on the biometric token, a validation attempt record that stores information associated with a validation attempt on the biometric token.

34. The wearable device of claim 33 wherein the processing circuitry being configured to invalidate the biometric token comprises the processing circuitry configured to perform at least one of the following in response to detecting or determining that an invalidating event has occurred for the biometric token:
store information in the memory indicating that the biometric token is invalid; and/or
delete, from the memory, at least a portion of the biometric token so as to render to biometric token invalid.

* * * * *